United States Patent [19]
Maruyama et al.

[11] Patent Number: 6,127,167
[45] Date of Patent: *Oct. 3, 2000

[54] METHOD OF CONTROLLING PROLIFERATION OF AEROBE

[75] Inventors: Shigeru Maruyama; Takuya Sato; Akio Yamamoto; Yuichiro Tanaka, all of Wako, Japan

[73] Assignee: Honda Giken Kogyo Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/670,989

[22] Filed: Jun. 28, 1996

Related U.S. Application Data

[63] Continuation of application No. 08/359,201, Dec. 19, 1994, abandoned.

[30] Foreign Application Priority Data

Dec. 28, 1993 [JP] Japan ................................. 5-334518

[51] Int. Cl.$^7$ ............................... C12N 1/00; C12N 1/20; B09B 3/00

[52] U.S. Cl. ....................... 435/262.5; 210/600; 210/601; 210/757; 210/758; 435/243; 435/244; 435/252.1; 435/262.5

[58] Field of Search ..................................... 435/243, 244, 435/252.1, 262.5, 822; 210/600, 601, 757, 758

[56] References Cited

U.S. PATENT DOCUMENTS

| | | | |
|---|---|---|---|
| 2,098,962 | 11/1937 | Hellbach et al. | 435/243 |
| 3,133,003 | 5/1964 | Schaefer et al. | 195/81 |
| 4,018,649 | 4/1977 | Cone, Jr. | 195/1.8 |
| 4,520,072 | 5/1985 | Yoshino et al. | 428/403 |
| 4,751,068 | 6/1988 | Bickar et al. | 423/437 |
| 5,143,710 | 9/1992 | Sawyer et al. | 423/581 |
| 5,200,092 | 4/1993 | Richards et al. | 210/758 |
| 5,336,431 | 8/1994 | Richards et al. | 252/184 |
| 5,389,356 | 2/1995 | Aust et al. | 423/659 |

FOREIGN PATENT DOCUMENTS

| | | | |
|---|---|---|---|
| 0210173 | 5/1984 | Australia | 435/244 |
| 6192563 | 5/1986 | Australia | 435/243 |
| 3515670 | 11/1986 | Australia | 435/252.1 |
| 59179065 | 10/1984 | Japan | 435/252.1 |
| 1310797 | 12/1989 | Japan . | |
| 2227191 | 9/1990 | Japan . | |
| 4-71483 | of 1992 | Japan . | |
| 2159834 | 12/1985 | United Kingdom | 435/252.1 |

OTHER PUBLICATIONS

Menezes et al., "Photodynamic Action . . . ", 1990, pp. 505–517.
Pantani et al., "Determination of BOD . . . ", 1973, 15(4), Abst.
Hoover et al., "Biochemical Oxidation . . . ", 1952, pp. 1144–1149.
Kalab, D., "Photodynamic Inactiv . . . ", 1967, pp. 181–182.
Knaff et al., "Cytochrome B & Photosyn . . . ", 1975, pp. 549–560.
FEBS Lett., Pudek et al., "Trapping of an intermed", 1976, pp. 330–333.
Bitton, Gabriel, "Wastewater Microbiology", Wiley–Liss, New York, pp. 147–166, May 18, 1994.
Brown, D., Hitz, H.R., and Schafer, L. "The Assessment of the Possible Inhibitory Effect of Dyestuffs on Aerobic Wastewater Bacteria Experience with a Screening Test", Chemosphere vol. 10, No. 3, pp. 245–261, Jan. 1981.
Hiraishi, A., "Respiratory quinone profiles as tools for identifying different bacterial populations in 'activated' sludge", (abstract) J. Gen. Appl. Microbiol. vol. 34, No. 1, pp. 39–56, Feb. 1988.
Hiraishi, A. and Komagata, K., "Isolation of Rhodoquinone–Containing Chemoorganotrophic Bacteria from Activated Sludge", FEMS Microbiol. Letters 58, pp. 55–58, Mar. 14, 1989.
Hiraishi, A., Masamune, K. and Kitamura, H., "Characterization of the Bacterial Population Structure in an Anaerobic–Aerobic Activated Sludge System on the Basis of Respiratory Quinone Profiles", Appl. Environ. Microbiol. vol. 55, No. 4, pp. 897–901, Apr. 1989.
Hiraishi, A., Shin, Y.K., and Sugiyama, J. "Brachymonas demitriflicans gen. nov., and aerobic chemoorganotrophic bacterium which contains rhodoquinones, and evolutionary relationships of rhodoquinone producers to bacterial species with various quinone classes", (abstract) J. Gen. Appl. Microbiol. vol. 41, No. 2, pp. 99–117, Apr. 1995.
Hu, H.Y., Nakagome, H., Fuji, K. and Urano, K., "The structural analysis of bacterial phase in an aerobic submerged biofilter on the basis of quinone profiles" (abstract) Mizu Kankyo Gakkaishi vol. 15, No. 4, pp. 262–265, (1992), Apr. 1992.
Ingrahm, J., Maaloe, O., and Neidhardt, F., "Growth of the Bacterial Cell", Sinauer Assoc., Inc., Sunderland, Mass., pp. 145–147, (1983), Jun. 30, 1983.
Hu, H., Fujie, K. and Urano, K., "Dynamic behaivor of aerobic submerged biofilter", (abstract) Water Sci Technol., vol. 28, No. 7, pp. 179–185, Mar. 16, 1994.

(List continued on next page.)

*Primary Examiner*—David M. Naff
*Assistant Examiner*—Deborah K. Ware
*Attorney, Agent, or Firm*—Lyon & Lyon LLP

[57] ABSTRACT

Disclosed herein is a method of controlling the proliferation of an aerobe, in which in the continuous culture of the aerobe by supplying a substrate and oxygen to a culture tank of the aerobe to cause the aerobe to decompose the substrate, the proliferation of the aerobe is inhibited while retaining the substrate-decomposing activity inherent in the aerobe. An oxidation-reduction substance which is reduced by electrons donated by an electron transport system of the aerobe and oxidized by oxygen supplied to the culture tank is caused to coexist with the aerobe in the culture tank.

11 Claims, 3 Drawing Sheets

OTHER PUBLICATIONS

Nakamura, K., Hiraishi, A., Yoshimi, Y., Kawaharasaki, M., Masuda, K. and Kamagata, Y. "Microlunatus phosphovorus gen. nov., sp. nov., a New gram–positive polyphosphate–accumulating bacterium isolated from activated sludge", International J. of Systematic Bact., vol. 45, pp. 17–22, Jan. 1995.

Rodriquez, G., Phipps, D., Ishiguro, K., and Ridgway, H.F., "Use of a Fluorescent Redox Probe for Direct Visualization of Actively Respiring Bacteria." Appl. Environ. Microbiol. vol. 58, No. 6, pp. 1801–1808, (Jun. 1992).

Stanier, R., Ingrahm, J., Wheelis, M. and Painter, P., "The Microbial World," 5th Ed. Prentice Hall, New Jersey, pp. 78–101, Feb. 7, 1986.

Wistreich, G. and Lechtman, M., "Microbiology", 3rd Ed., Glencoe Publishing Co. Inc., Encino, California, pp. 764–786, Apr. 28, 1980.

English language abstract of JP 1–310797 and 2–227191, Dec. 1989, Sep. 1990, respectively.

Gaudy et al. "Microbiology for Environmental Scientists and Engineers" McGraw Hill May 7, 1980.

Pantani et al. Determination for Biochemical Oxygen Demand and of Associated Parameters (Translation into English of the following article "Determinazione Della Richiesta Biochimica Di Ossigeno e Di Parametri Ad Essa Correlati", *Inquinamento*, 15(4), pp. 12–17 (1973), Jul. 1973.

McGrath et al., *Nature*, vol. 212, pp. 534–535, Oct. 29, 1966.

METHOD OF CONTROLLING PROLIFERATION OF AEROBE

The application is a continuation of application Ser. No. 08/359,201, filed Dec. 19, 1994, now abandoned.

BACKGROUND OF THE INVENTION

1. Field of the Invention

The present invention relates to a method of controlling the proliferation of an aerobe, in which in the continuous culture of the aerobe by supplying a substrate and oxygen to a culture tank of the aerobe to cause the aerobe to decompose the substrate, the proliferation of the aerobe is inhibited while retaining the substrate-decomposing activity inherent in the aerobe.

2. Description of the Background Art

The culture of an aerobe, in particular, continuous culture has heretofore been used as an activated sludge process in a treating tank for purifying waste water such as, for example, organic sewage. In this activated sludge process, excess sludge is formed in a relatively great amount with the progress of the continuous culture of the aerobe, and most of such excess sludge is treated as industrial waste.

However, the industrial waste has been requested to decrease to a great extent from the viewpoint of environmental protection and in view of the trend of society. If only the proliferation of the aerobe can be inhibited without lowering the substrate-decomposing activity (purifying function) inherent in the aerobe, both reduction in treatment cost and decrease of industrial waste can be achieved. Such a method is hence extremely advantageous.

According to the activated sludge process, as illustrated in FIG. 1, waste water to be treated, which contains pollutant organic substances (substrate), is first adjusted to a pH, at which an aerobe is easy to act, in an adjustment tank 1 and then supplied to an aeration tank 2 in which the aerobe is being cultured. Air containing oxygen is supplied to the aeration tank 2 from a source of air supply 4, which is attached thereto, so as to aerate the aeration tank 2, whereby the pollutant organic substances (substrate) contained in the waste water is oxidatively decomposed by the action of the aerobe. In this case, a part of the organic substances is removed in the form of carbon dioxide by the substrate-decomposing action of the aerobe in the aeration tank 2, and at the same time, the aerobe proliferates to form an agglomerate (activated sludge). A part of the agglomerate is then discharged into a settling tank 3 together with the waste water purified.

In the settling tank 3, the agglomerate is precipitated and separated from the purified waste water, and the purified waste water is discharged as treated water from the settling tank 3. On the other hand, most of the agglomerate separated is discharged as excess sludge through a discharge duct 5 to treat it. The remainder of the agglomerate is returned as return sludge to the aeration tank 2 through a conduit 6 branched off from the discharge conduit 5.

In the activated sludge process, the amount of the excess sludge formed increases when the aerobe is continuously cultured in the aeration tank 2. Therefore, it is necessary to treat the excess sludge as industrial waste. As a method of treating the excess sludge, Japanese Patent Application Laid-Open No. 227191/1990 discloses a technique in which an alkaline substance is added to excess sludge, from which return sludge has been removed, to dissolve aerobes contained therein, thereby decreasing the excess sludge.

However, the use of the alkaline substance as described above raises the pH of waste water after the activated sludge treatment. Therefore, an additional treating step is required for the pH adjustment and the like, resulting in unavoidable increase in cost. There is hence a demand for development of a technique capable of controlling the amount of excess sludge itself to be formed without subjecting the excess sludge to a special treatment.

In order to control the amount of the excess sludge to be formed, it has heretofore been conducted to regulate the amount of the return sludge returned to the aeration tank 2 or control the amount of oxygen-containing air to be supplied to the aeration tank 2 from the source of air supply 4 according to the concentration of pollutant organic substances contained in waste water to be fed to the aeration tank 2.

According to this method, however, the substrate-decomposing action of the aerobe in the aeration tank 2 is hindered though the amount of the excess sludge to be formed can be controlled. Such a method therefore involves a disadvantage that waste water treatment, which is the original object of the activated sludge process, is not sufficiently performed. In addition, the conventional methods cannot control the proliferation itself of the aerobe, and is hence not said to essentially control the amount of the excess sludge to be formed.

SUMMARY OF THE INVENTION

It is an object of the present invention to provide a method of controlling the proliferation of an aerobe, which can solve such disadvantages and inhibit the proliferation of the aerobe while retaining the substrate-decomposing action inherent in the aerobe.

In order to achieve the above object, in an aspect of the present invention, there is thus provided a method of controlling the proliferation of an aerobe, in which in the continuous culture of the aerobe by supplying a substrate and oxygen to a culture tank of the aerobe to cause the aerobe to decompose the substrate, the proliferation of the aerobe is inhibited while retaining the substrate-decomposing activity inherent in the aerobe, wherein an oxidation-reduction substance which is reduced by electrons donated by an electron transport system of the aerobe and oxidized by oxygen supplied to the culture tank is caused to coexist with the aerobe in the culture tank.

Other objects, features and advantages of the present invention will be readily appreciated from the preferred embodiments of the present invention, which will be described subsequently in detail with reference to the accompanying drawings.

DETAILED DESCRIPTION OF THE PREFERRED EMBODIMENTS

The present invention will hereinafter be described by preferred embodiments.

When waste water containing a substrate, and oxygen are supplied to a culture tank of an aerobe, the substrate is decomposed by the aerobe finally into carbon dioxide and water. On the other hand, the aerobe aerobically respires to acquire energy for life activities from the decomposition products of the substrate and proliferate.

The mechanism of acquiring the energy by the aerobic respiration is explained taking the case of carbohydrate as a respiration substrate. It is composed of a glycolytic pathway, a TCA cycle and an electron transport system. In the glycolytic pathway and the TCA cycle, hydrogen is first generated in the course of further decomposing the carbohydrate obtained by the decomposition of a pollutant organic substance into various organic acids, and is transferred to the electron transport system.

Figure 2:
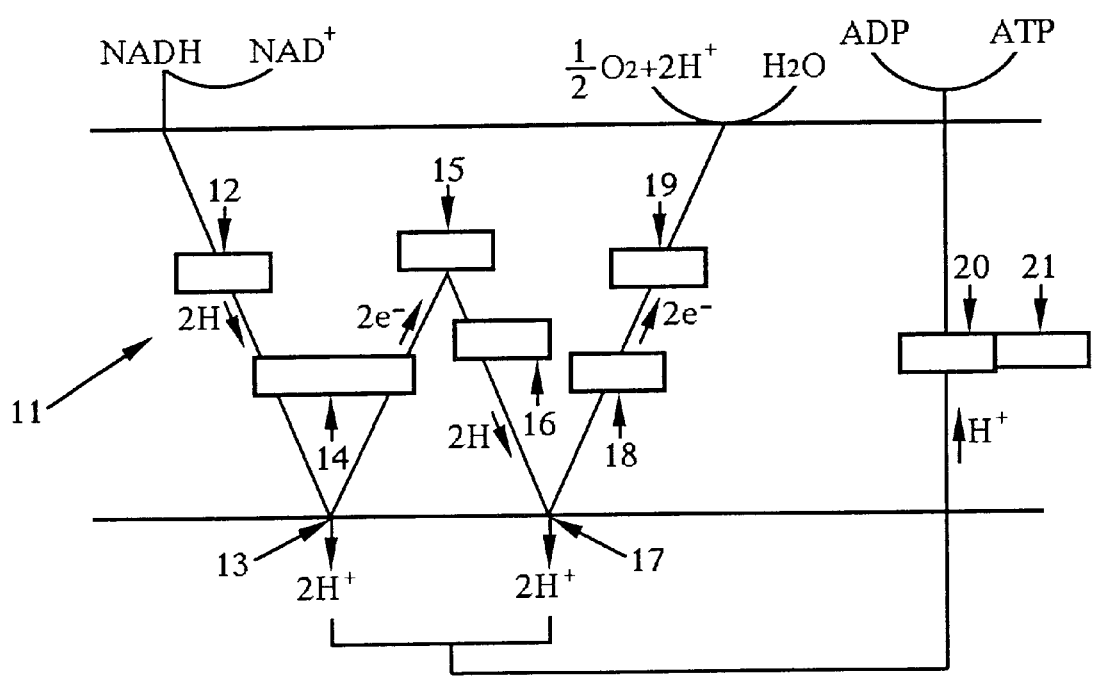
FIG. 2 illustrates an electron transport system in an aerobic respiration system taking the case of *Escherichia coli*.

In the electron transport system, as illustrated in FIG. 2 taking the case of *Escherichia coli,* $NAD^+$(oxidized nicotinamide adenine dinucleotide) first accepts hydrogen generated by the decomposition of the substrate in the TCA cycle and the like on the inside of a cell membrane 11, whereby NADH (reduced nicotinamide adenine dinucleotide) is formed. Two hydrogen atoms are then taken away from NADH by a membrane bound protein 12 to form $NAD^+$ again.

The two hydrogen atoms taken away are transferred on the outside of the cell membrane 11 by the membrane bound protein 12 and separated into two hydrogen ions and two electrons there. This charge separation is a coupled reversible reaction as represented by the following reaction formula (1). Thus, a position at which the reversible reaction is conducted is called a coupling site 13.

$$2H = 2H^+ + 2e^- \qquad (1)$$

At the coupling site 13, only two electrons formed by the charge separation are transferred by an FeS protein 14 to a membrane bound protein 15 on the inside of the cell membrane 11. As a result, the two hydrogen ions formed by the charge separation are left on the outside of the cell membrane 11. Therefore, the hydrogen ion concentration on the outside of the cell membrane 11 becomes higher than that on the inside of the cell membrane 11, whereby a concentration gradient of proton is formed.

The membrane bound protein 15 draws two hydrogen ions on the inside of the cell membrane 11 as hydrogen atoms by the two electrons donated from the FeS protein 14 and transfers these hydrogen atoms to coenzyme Q 16 (ubiquinone). Since the coenzyme Q 16 is a hydrogen carrier and also a hydrophobic compound, it can freely move in the cell membrane 11 and causes the hydrogen atoms to separate into electrons and hydrogen ions on the outside of the cell membrane 11 as described above so as to release them. The coupled reversible reaction represented by the reaction formula (1) also takes place here. Therefore, the position is called a coupling site 17.

The two electrons released from the coenzyme Q 16 at the coupling site 17 are transferred on the inside of the cell membrane 11 by cytochrome b 18 and cytochrome o 19 this time, thereby synthesizing a water molecule from a half molecule of oxygen and two hydrogen ions. In-the coupling site 17, the two hydrogen ions formed by the charge separation are left on the outside of the cell membrane 11, whereby the concentration gradient of proton is further increased.

Namely, in the electron transport system, NADH is oxidized into $NAD^+$ on the inside of the cell membrane 11, and at the same time a water molecule is synthesized. On the other hand, four hydrogen ions are pumped out on the outside of the cell membrane 11, thereby forming the concentration gradient of proton.

By the way, ATPase $F_o$ 20 exists in the cell membrane 11, and ATPase $F_1$ 21 couples to the ATPase $F_0$ 20 on the inside of the cell membrane 11. Since the concentration gradient of proton has energy by itself, the hydrogen ions pumped out move on the inside of the cell membrane 11 through the ATPases $F_0$ 20 and $F_1$ 21 and are used in a reaction in which ATP (adenosine triphosphate) is synthesized from ADP (adenosine diphosphate) and phosphoric acid. This ATP is used in vital maintenance and an active source for synthesis (source for proliferation) as a source of energy for life activities.

According to the method of the present invention, the oxidation-reduction substance coexists with the aerobe in the culture tank. Therefore, in the electron transport system, the electrons formed by the charge separation at the coupling site 13 or the coupling site 17 are donated to the oxidation-reduction substance. As a result, the concentration gradient of proton formed in the above-described manner becomes insufficient, and so the synthesis of ATP in the electron transport system is inhibited. ATP synthesized in the electron transport system accounts for about 70% of ATP formed in the whole aerobic respiration system. Therefore, if the synthesis of ATP in the electron transport system is inhibited, ATP is lacking, and so the proliferation is inhibited.

On the other hand, the oxidation-reduction substance is turned to a reduced form by the donation of the electrons in the above-described manner. However, it is oxidized by oxygen being supplied to the culture tank, whereby it is returned to the oxidized form. Therefore, the oxidation-reduction substance is used repeatedly in the action to accept the electrons from the electron transport system.

According to the present invention, therefore, only the proliferation of the aerobe can be inhibited while retaining the substrate-decomposing activity inherent in the aerobe.

The oxygen used may be supplied in the form of a mixture with other one or more gases. Air is generally supplied as a gas containing oxygen. Preferable examples of the aerobe include aerobic bacteria, facultative anaerobic bacteria, actinomycete, yeast, mold and basidiomycete. These aerobes may be used either singly or in any combination thereof.

When the oxidation-reduction potential of the oxidation-reduction substance falls within a range of from −150 to +150 mV based on a normal hydrogen electrode (NHE), the proliferation of the aerobe can be efficiently inhibited. However, the aerobe is not limited to such aerobes, and any aerobe may be used so far as it can mediate the electron transfer between components of aerobic respiration system in the aerobe, cytochromes and the like and oxygen, and is oxidized by oxygen.

In the method of the present invention, the oxidation-reduction substances having an oxidation-reduction potential within the above range may be used either singly or in any combination thereof. If the oxidation-reduction substances are used singly, the proliferation of the aerobe can be efficiently inhibited when one selected from, for example, the group consisting of thionine (formula 2), Safranine-O (formula 3), New Methylene Blue (formula 4), Meldola's Blue (formula 5), Methylene Blue (formula 6), Toluidine Blue (formula 7), Azure-A (formula 8), phenazine methosulfate (formula 9) and hydroxynaphtoquinone (formula 10) represented by the following structural formulae (2) to (10), respectively, of the oxidation-reduction substances having an oxidation-reduction potential within the above range is used.

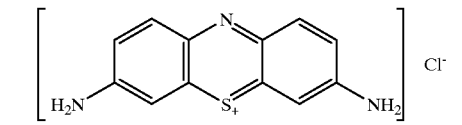 (2)

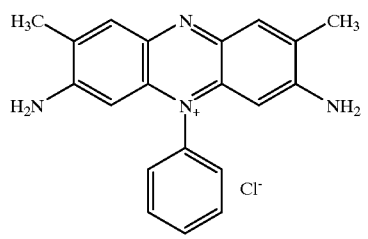 (3)

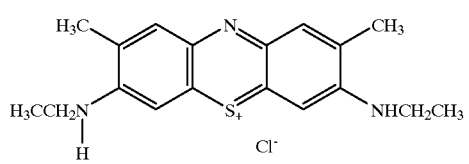 (4)

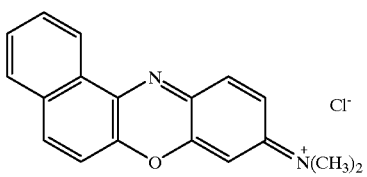 (5)

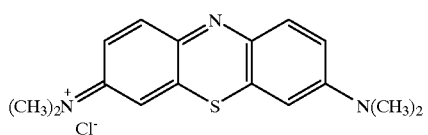 (6)

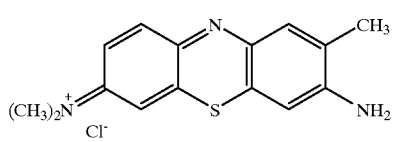 (7)

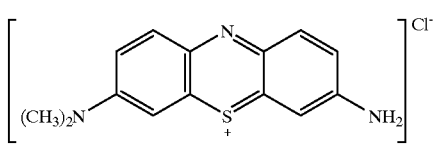 (8)

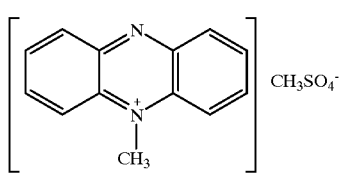 (9)

-continued

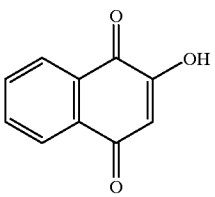 (10)

As the oxidation-reduction substances, dyes having a hydrophobic side chain and a hydrophilic side chain on their phenothiazine skeletons [represented by the following structural formula (11)], such as thionine and New Methylene Blue, are particularly suitable. These dyes have good affinity for the cell membrane, which brings about an effect that an electron becomes easy to be emitted to oxygen.

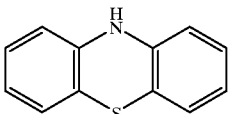 (11)

If a plurality of the oxidation-reduction substances is used in combination, the combined use of, for example, thionine and Safranine-O of the oxidation-reduction substances having an oxidation-reduction potential within the above range permits the uptake of the electrons in a wider potential range, and can obtain an effect of inhibiting the proliferation of the aerobe like the single use of the oxidation-reduction substance.

Further, the oxidation-reduction substance may preferably be used in a concentration ranging from 1 to 50 $\mu$M in the culture tank because the proliferation of the aerobe can be efficiently inhibited. If the concentration of the oxidation-reduction substance is less than 1 $\mu$M in the culture tank, the effect of inhibiting the proliferation of the aerobe cannot be sufficiently brought about. On the other hand, the use of the oxidation-reduction substance in a concentration exceeding 50 $\mu$M cannot obtain more effect correspondingly.

The oxidation-reduction substance may be used with the oxidation-reduction substance dissolved in waste water in the culture tank or supported on a carrier such as styrene beads, thereby recovering it with ease. When the oxidation-reduction substance is used in the form of a solution in the waste water to be treated in the culture tank without supporting it on the carrier, it can be adsorbed on an adsorbent such as active carbon before discharging the treated waste water, thereby recovering it with more ease.

As an example of the culture tank of the aerobe used in the method of the present invention, may be mentioned a treating tank for organic sewage. In the treating tank for organic sewage, pollutant organic substances contained in the organic sewage are decomposed as a substrate by the aerobe. Therefore, the concentration of the organic substances in the organic sewage can be reduced, and moreover the proliferation of the aerobe can be inhibited.

The method of controlling the proliferation of an aerobe according to present invention will hereinafter be described in more detail by reference to the drawings.

Figure 1:
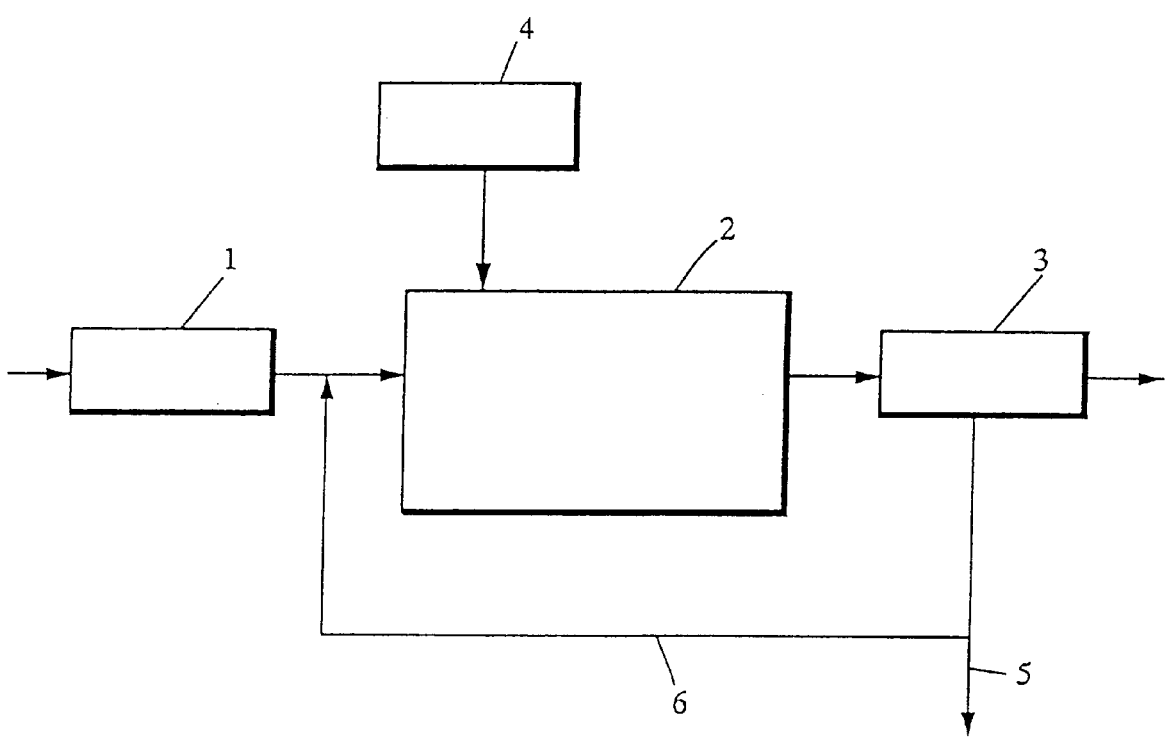
FIG. 1 illustrates an exemplary construction of an activated sludge process equipment for waste water.
Figure 3:
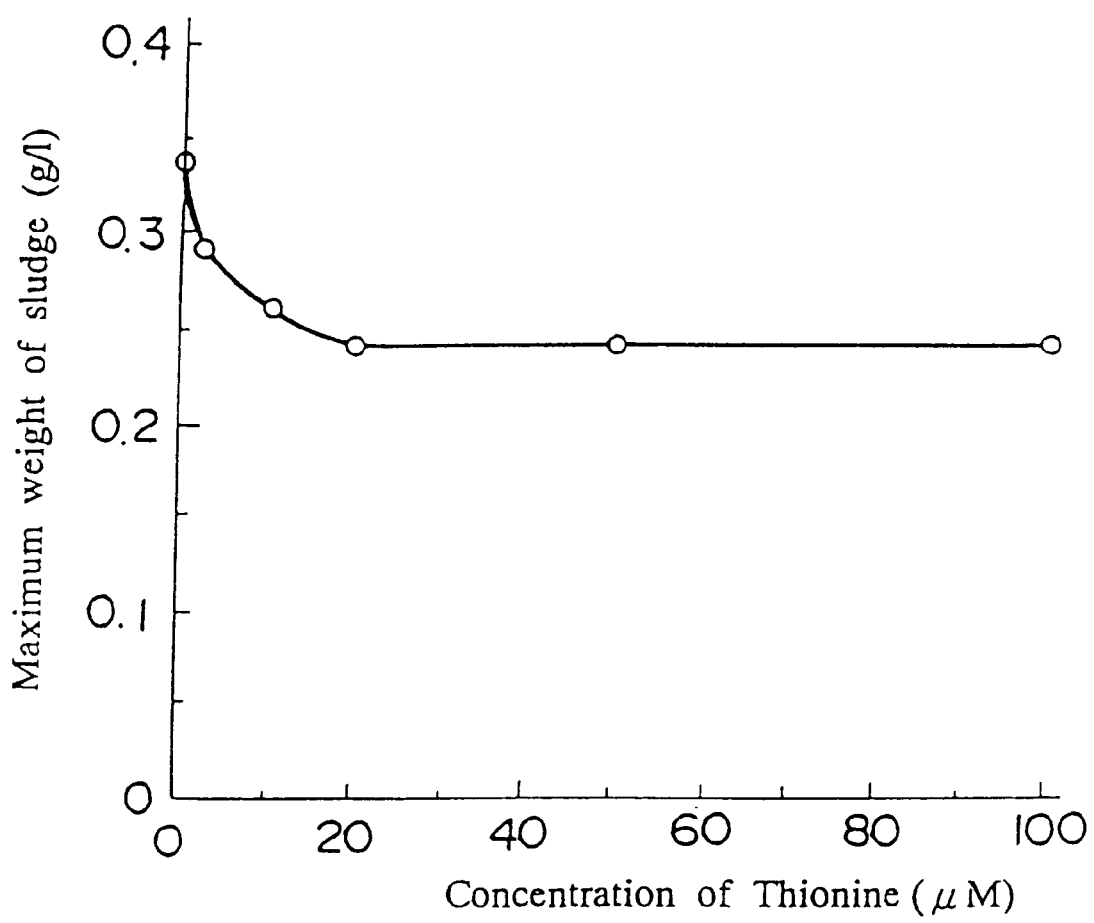
FIG. 3 diagrammatically illustrates the relationship between the concentration of an oxidation-reduction substance and the proliferation of an aerobe in a culture tank.

FIG. 1 illustrates an exemplary construction of an activated sludge process equipment for waste water, which is used in this embodiment, FIG. 2 illustrates an electron transport system in an aerobic respiration system of a living body taking the case of *Escherichia coli,* and FIG. 3 diagrammatically illustrates the relationship between the concentration of an oxidation-reduction substance and the proliferation of an aerobe in a culture tank.

As illustrated in FIG. 1, an activated sludge process equipment for waste water according to this embodiment includes an adjustment tank 1 in which the pH of waste water (organic sewage) to be treated is adjusted, an aeration tank 2 in which an aerobe is being cultured, and the waste water supplied from the adjustment tank 1 is treated with the aerobe, and a settling tank 3 in which an agglomerate of the aerobe (activated sludge) contained in the treated waste water fed from the aeration tank 2 is precipitated, and only purified waste water is discharged therefrom. A source of air supply 4 from which air containing oxygen is supplied to the aeration tank 2 so as to aerate the aeration tank 2 is attached to the aeration tank. The settling tank 3 has a discharge conduit 5 through which the separated agglomerate is discharged as excess sludge, and a conduit 6 branched off from the discharge conduit 5, through which a part of the agglomerate is returned as return sludge to the aeration tank 2. In the activated sludge process equipment for waste water according to this embodiment, thionine is dissolved as an oxidation-reduction substance together with the aerobe in the waste water in the aeration tank 2.

The thionine is an oxidation-reduction substance which is reduced by electrons donated by the electron transport system of the aerobe and oxidized by oxygen in the air supplied to the aeration tank 2, and is dissolved to give a concentration ranging from 1 to 50 $\mu$M in the aeration tank 2.

In the activated sludge process equipment for waste water according to this embodiment, the organic sewage as the waste water is first supplied to the adjustment tank 1 and adjusted to a pH at which an aerobe is easy to act. The organic sewage is then supplied to the aeration tank 2 in which the aerobe is being cultured. The pollutant organic substances (substrate) contained in the organic sewage is then oxidatively decomposed by the action of the aerobe, and the treated and purified waste water is discharged through the settling tank 3.

Air containing oxygen is supplied to the aeration tank 2 from the source of air supply 4 so as to aerate the aeration tank 2, where a part of the organic substances are used in proliferation of the aerobe by the aerobic respiration of the aerobe, and the agglomerate (activated sludge) is formed from the aerobe proliferated.

In this time, thionine, which is an oxidation-reaction substance, exists in the form of the solution together with the aerobe in the aeration tank 2. Therefore, electrons are donated to thionine at the coupling site 13 in the electron transport system illustrated in FIG. 2, upon the aerobic respiration of the aerobe. As a result, the electrons are not transferred beyond the coupling site 13 in the electron transport system illustrated in FIG. 2, whereby the synthesis of ATP is inhibited, and so the proliferation of the aerobe is inhibited.

The amount of the excess sludge which is precipitated and separated in the settling tank 3 and discharged through the discharge conduit 5 is therefore reduced, resulting in easy treatment. Incidentally, thionine turned to the reduced form by the acceptance of the electrons is oxidized with oxygen in the air supplied to the aeration tank 2 and returned to the oxidized form. Therefore, the thionine can be used repeatedly in the action to accept the electrons at the coupling site 13.

In the activated sludge process equipment, since thionine exists in the form dissolved in the treated and purified waste water to be discharged from the settling tank 3, it is recovered by means of an adsorbent such as active carbon prior to the discharging. The thionine may be used in the following manner. Namely, it is supported on a carrier such as active carbon or styrene beads in advance, and the thus-supported thionine is suspended in the aeration tank 2 or fixed to the wall of the aeration tank 2 or an insert. This makes the recovery of thionine easier.

In this embodiment, thionine is used by itself. However, it may be used in combination with another oxidation-reduction substance, for example, Safranine-O. The kind of an aerobe used in purification of waste water may vary according to the kind of the waste water. The combined use of the plural oxidation-reduction substances as described above permits the uptake of electrons from the electron transport system in a wider potential range, and hence can adapt to various kinds of waste water.

Proliferative experiments as to *Escherichia coli* and activated sludge carried out in accordance with the method of controlling the proliferation of an aerobe according to the present invention will then be described.

The experiment as to *Escherichia coli* is first described. A Sakaguchi flask containing 135 ml of a medium which contained a nutrient composed of 1 g/l of glucose, and inorganic salts for adjusting osmotic pressure and the like, and another Sakaguchi flask containing 135 ml of a medium with 0.387 mg of thionine further dissolved in the above-described medium were provided. In the medium in each flask, were inoculated 15 ml of a starter culture of *Escherichia coli*. As a result, the concentration of thionine in the medium in which thionine had been dissolved was finally 10 $\mu$M. Both flasks were then subjected to shaking culture (135 rpm) at 30° C.

The concentration of glucose, which was an nutrient component in the medium in each flask, was determined by means of a glucose assay kit (Glucose Test Wako, trade name, product of Wako Pure Chemical Industries, Ltd.) before and after the proliferation by the culture. Besides, the cell count when proliferated to the greatest extent upon the culture was measured by a spectrophotometer to determine the percent inhibition of proliferation (%). The percent inhibition of proliferation (%) is expressed by the following equation:

$$\text{Percent inhibition of proliferation}(\%) = \frac{\text{Cell count in Medium } A - \text{Cell count in Medium } B}{\text{Cell count in Medium } A} \times 100$$

wherein Medium A means the medium containing no thionine, and Medium B denotes the medium with thionine caused to coexist therein. The results are shown in Table 1.

TABLE 1

|  | Concentration of glucose (g/l) | | Cell count of *Escherichia coli* ($OD_{660}$) | Percent inhibition (%) |
| --- | --- | --- | --- | --- |
|  | Before culture | After proliferation | | |
| Medium A | 1.15 | 0 | 1.04 | — |
| Medium B | 1.08 | 0.02 | 0.88 | 15.4 |

The experiment as to activated sludge is then described. A Sakaguchi flask containing 135 ml of a medium which contained a nutrient composed of 0.475 g/l of peptone and 0.313 g/l of meat extract, and inorganic salts for adjusting osmotic pressure and the like, and another Sakaguchi flask containing 135 ml of a medium with 0.387 mg of thionine further dissolved in the above-described medium were provided. In the medium in each flask, were inoculated 15 ml of a starter culture of the activated sludge. As a result, the concentration of thionine in the medium in which thionine had been dissolved was finally 10 μM. Both flasks were then subjected to shaking culture (135 rpm) at 30° C.

The concentrations of peptone and meat extract, which were nutrient components in the medium in each flask, were determined by means of a total organic carbon meter (TOC500, trade name, manufactured by Shimadzu Corporation) before and after the proliferation by the culture. Besides, the cell weight when proliferated to the greatest extent upon the culture was determined in terms of dry weight to find the percent inhibition of proliferation (%). The percent inhibition of proliferation (%) is expressed by the following equation:

$$\text{Percent inhibition of proliferation (\%)} = \frac{\text{Cell weight in Medium } A - \text{Cell weight in Medium } B}{\text{Cell weight in Medium } A} \times 100$$

wherein Medium A means the medium containing no thionine, and Medium B denotes the medium with thionine caused to coexist therein. The results are shown in Table 2.

TABLE 2

| | Concentration of total organic carbon (ppm) | | Cell weight of activated sludge (g/l) | Percent inhibition (%) |
|---|---|---|---|---|
| | Before culture | After proliferation | | |
| Medium A | 249.2 | 8.2 | 0.37 | — |
| Medium B | 254.3 | 18.3 | 0.25 | 32.4 |

As apparent from Tables 1 and 2, it is understood that the degree of consumption of the nutrient is substantially equal irrespective of the coexistence of thionine in the medium, and the coexistence of thionine in the medium does not inhibit the substrate-decomposing activities of the aerobes, but inhibits the proliferation of the *Escherichia coli* and activated sludge. Incidentally, the value of the percent inhibition allows a latitude of ±10% or so because individuals of *Escherichia coli* and activated sludge vary in biological reaction even when experimental conditions are kept constant, and errors in measurement may arise according to how to measure.

The same experiment as to *Escherichia coli* as described above was then carried out using substances other than thionine as the oxidation-reduction substance. The oxidation-reduction potentials of thionine and the other oxidation-reduction substances based on a normal hydrogen electrode, and the percent inhibition of proliferation are shown in Table 3. The percent inhibition (%) is expressed by the following equation:

$$\text{Percent inhibition (\%)} = \frac{\text{Cell count in Medium } A - \text{Cell count in Medium } B}{\text{Cell count in Medium } A} \times 100$$

wherein Medium A means the medium containing no oxidation-reduction substance, and Medium B denotes the medium with thionine or another oxidation-reduction substance caused to coexist therein.

TABLE 3

| | Oxidation-reduction potential (mV) | Percent inhibition (%) |
|---|---|---|
| Meldola's Blue | 110 | 35 |
| Phenazine methosulfate | 65 | 26 |
| Thionine | 23 | 35 |
| Toluidine Blue | 3 | 28 |
| Azure-A | −5 | 27 |
| Methylene Blue | −15 | 29 |
| Safranine-O | −20 | 37 |
| New Methylene Blue | −20 | 35 |
| Hydroxynaphtoquinone | −130 | 28 |

As apparent from Table 3, it is understood that the oxidation-reduction substances each having an oxidation-reduction potential ranging from −130 to +110 mV based on the normal hydrogen electrode have an effect of inhibiting the proliferation of *Escherichia coli*. Incidentally, any oxidation-reduction substance can bring about the same effect as the oxidation-reduction substances shown in Table 3 so far as it has an oxidation-reduction potential ranging from −150 to +150 mV based on the normal hydrogen electrode.

A Sakaguchi flask containing 135 ml of a medium which contained a nutrient composed of 0.475 g/l of peptone and 0.313 g/l of meat extract, and inorganic salts for adjusting osmotic pressure and the like, another Sakaguchi flask containing 135 ml of a medium with 0.774 mg of thionine further dissolved in the first-mentioned medium, a further Sakaguchi flask containing 135 ml of a medium with 1.01 mg of Safranine-O further dissolved in the first-mentioned medium, and a still further Sakaguchi flask containing 135 ml of a medium with 0.387 mg of thionine and 0.505 mg of Safranine-O further dissolved in the first-mentioned medium were then provided. In the medium in each flask, were inoculated 15 ml of a starter culture of activated sludge. As a result, the concentration of the oxidation-reduction substance in either the medium in which thionine or Safranine-O had been dissolved by itself, or the medium in which thionine and Safranine-O had been dissolved in combination was finally 20 μM. All the flasks were then subjected to shaking culture (135 rpm) at 30° C.

The concentrations of peptone and meat extract, which were nutrient components in the medium in each flask, were determined by means of a total organic carbon meter (TOC500, trade name, manufactured by Shimadzu Corporation) before and after the proliferation by the culture. Besides, the cell weight when proliferated to the greatest extent upon the culture was determined in terms of dry weight to find the percent inhibition of proliferation (%). The percent inhibition of proliferation (%) is expressed by the following equation:

$$\text{Percent inhibition of proliferation (\%)} = \frac{\text{Cell weight in Medium } A - \text{Cell weight in Medium } B}{\text{Cell weight in Medium } A} \times 100$$

wherein Medium A means the medium containing no oxidation-reduction substance, and Medium B denotes the medium with the oxidation-reduction substance caused to coexist therein. The results are shown in Table 4.

TABLE 4

| | Concentration of total organic carbon (ppm) | | Cell weight of activated sludge (g/l) | Percent inhibition (%) |
|---|---|---|---|---|
| | Before culture | After proliferation | | |
| Medium A | 239.7 | 14.1 | 0.37 | — |
| Medium B | | | | |
| Thio | 241.8 | 21.2 | 0.30 | 18.9 |
| Safrn | 241.2 | 17.9 | 0.31 | 16.2 |
| Thio, Safrn | 240.5 | 22.9 | 0.30 | 18.9 |

(Note) Thio: Thionine; Safrn: Safranine-O.

As apparent from Table 4, it is understood that the combined use of plural oxidation-reduction substances brings about the same effect as the case where the oxidation-reduction substance is used by itself.

A Sakaguchi flask containing 135 ml of a medium which contained a nutrient composed of 0.475 g/l of peptone and 0.313 g/l of meat extract, and inorganic salts for adjusting osmotic pressure and the like, and other Sakaguchi flasks separately containing 135 ml of media with thionine further dissolved in varied amounts ranging from 0.077 to 3.88 mg in the above-described medium were then provided. In the medium in each flask, were inoculated 15 ml of a starter culture of the activated sludge. As a result, the flasks separately contained thionine in varied amounts ranging from 0 to 100 MM. All the flasks were then subjected to shaking culture (135 rpm) at 30° C. to determine the cell weight in terms of dry weight when proliferated to the greatest extent. The results are illustrated in FIG. 3.

As apparent from FIG. 3, it is understood that if the concentration of thionine is less than 1 $\mu$M in the flask, the effect of inhibiting the proliferation of the activated sludge cannot be sufficiently brought about, while the use of thionine in a concentration exceeding 50 $\mu$M cannot obtain more effect correspondingly.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for treating wastewater containing organic waste and aerobes, comprising:
   supplying oxygen to the wastewater; and
   adding to the wastewater an oxidation-reduction substance known to oxidize the aerobes and having an oxidation-reduction potential of −150 to +150 mV based on a normal hydrogen electrode, the oxidation-reduction substance being added in an amount wherein a concentration of the oxidation-reduction substance is between 1 and 50 $\mu$M whereby, =p1 the aerobes decompose at least a portion of the organic waste and the aerobes proliferate, thereby forming a sludge comprised of aerobes, and whereby
   electrons are transferred from at least a portion of the aerobes to the oxidation-reduction substance thereby decreasing the amount of aerobe proliferation that would otherwise occur in the absence of the oxidation-reduction substance.

2. A method for treating wastewater containing organic waste and aerobes, comprising:
   supplying oxygen to the wastewater;
   adding to the wastewater an oxidation-reduction substance known to oxidize the aerobes and having an oxidation-reduction potential of −150 to +150 mV based on a normal hydrogen electrode, the oxidation-reduction substance being added in an amount wherein a concentration of the oxidation-reduction substance is between 1 and 50 $\mu$M;
   decomposing at least a portion of the organic waste and proliferating the aerobes, thereby forming a sludge comprised of aerobes; and
   transferring electrons from at least a portion of the aerobes to the oxidation-reduction substance, thereby decreasing the amount of aerobe proliferation that would otherwise occur in the absence of the oxidation-reduction substance.

3. A method for treating wastewater containing organic waste and aerobes, comprising:
   supplying the wastewater and oxygen to an aeration tank;
   adding to the wastewater an oxidation-reduction substance known to oxidize the aerobes and having an oxidation-reduction potential of −150 to +150 mV based on normal hydrogen electrode, the oxidation-reduction substance being added in an amount wherein a concentration of the oxidation-reduction substance is between 1 and 50 $\mu$M;
   decomposing at least a portion of the organic waste and proliferating the aerobes, thereby forming treated water and forming a sludge comprised of aerobes;
   transferring electrons from at least a portion of the aerobes to the oxidation-reduction substance, thereby decreasing the amount of aerobe proliferation that would otherwise occur in the absence of the oxidation-reduction substance; and
   transporting the treated water and sludge to a settling tank wherein the treated water and sludge are separated.

4. The method according to claim 1, further comprising: recovering said oxidation-reduction substance by adsorbing said oxidation-reduction substance onto an adsorbent.

5. The method of claim 1, 2, or 3 further comprising: transferring electrons from the oxidation-reduction substance to the oxygen and transferring electrons from the aerobes to the oxidation-reduction substance.

6. The method of claim 5 further comprising: recycling the oxidation-reduction substance by repetitiously transferring electrons from the oxidation-reduction substance to the oxygen and transferring electrons from the aerobes to the oxidation-reduction substance.

7. The method of claim 1, 2, or 3 wherein the aerobes comprise facultative anaerobic microorganisms.

8. The method of claim 1, 2, or 3 wherein the oxidation-reduction substance is comprised of one or more oxidation-reduction substances.

9. The method of claim 1, 2, or 3 wherein the oxidation-reduction substance is selected from the group consisting of thioneine, Safranine-O, New Methylene Blue, Meldola's Blue, Methylene Blue, Toluidine Blue, Azure-A, phenazine methosulfate, and hydroxynaphtoquinone.

10. The method of claim 1, 2, or 3 wherein the oxidation-reduction substance is comprised of thioneine and Safranine-O.

11. The method of claim 1, 2, or 3 wherein the oxidation-reduction substance is supported on a carrier.

* * * * *